US 8,753,336 B2

(12) United States Patent
Kelly et al.

(10) Patent No.: US 8,753,336 B2
(45) Date of Patent: Jun. 17, 2014

(54) METHOD FOR INDIRECTLY ABLATING TISSUE USING IMPLANTED ELECTRODE DEVICES

(75) Inventors: Amy C. Kelly, San Francisco, CA (US); Robert J. Garabedian, Tyngsboro, MA (US); Steven K. Landreville, San Francisco, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 969 days.

(21) Appl. No.: 12/818,091

(22) Filed: Jun. 17, 2010

(65) Prior Publication Data

US 2010/0256633 A1    Oct. 7, 2010

Related U.S. Application Data

(63) Continuation of application No. 11/258,417, filed on Oct. 24, 2005, now Pat. No. 7,749,219, which is a continuation of application No. 10/387,892, filed on Mar. 13, 2003, now Pat. No. 6,979,330.

(51) Int. Cl.
*A61B 18/14* (2006.01)

(52) U.S. Cl.
USPC ............................................ 606/41; 607/101

(58) Field of Classification Search
USPC ............. 606/27–31, 41, 45–50; 607/101–102
See application file for complete search history.

(56) References Cited

U.S. PATENT DOCUMENTS

| | | | |
|---|---|---|---|
| 5,122,136 A | | 6/1992 | Guglielmi et al. |
| 5,354,295 A | * | 10/1994 | Guglielmi et al. .............. 606/32 |
| 5,385,579 A | | 1/1995 | Helland |
| 5,715,817 A | * | 2/1998 | Stevens-Wright et al. ... 600/373 |
| 5,919,187 A | * | 7/1999 | Guglielmi et al. .............. 606/32 |
| 5,980,514 A | | 11/1999 | Kupiecki et al. |
| 5,984,929 A | | 11/1999 | Bashiri et al. |
| 6,019,757 A | * | 2/2000 | Scheldrup ....................... 606/49 |
| 6,337,998 B1 | | 1/2002 | Behl et al. |
| 6,379,353 B1 | | 4/2002 | Nichols |
| 6,470,218 B1 | | 10/2002 | Behl |
| 7,294,123 B2 | | 11/2007 | Jones et al. |
| 2002/0198523 A1 | | 12/2002 | Behl |
| 2004/0181214 A1 | | 9/2004 | Garabedian et al. |

FOREIGN PATENT DOCUMENTS

| | | |
|---|---|---|
| WO | WO 96/29946 | 10/1996 |
| WO | WO 03/020138 | 3/2003 |

OTHER PUBLICATIONS

PCT International Search Report for PCT/US04/004680, Applicant: Scimed Life Systems, Inc., Forms PCT/ISA/210 and 220, dated Jul. 7, 2004 (7 pages).

(Continued)

*Primary Examiner* — Michael Peffley
(74) *Attorney, Agent, or Firm* — Kacvinsky Daisak Bluni PLLC

(57) ABSTRACT

Methods are provided for ablating tissue by implanting a plurality of electrode devices within the tissue to be treated and exposing the implanted electrode devices with RF energy conveyed from a separate electrode device. In this manner, a greater region of tissue is ablated than what would normally be ablated with the separate electrode device. In addition, the implanted electrode devices can create a roadmap that allows the progress of the treatment to be managed during follow-ups. The implanted electrode devices can be variously delivered to the tissue, for example, by detaching the electrode devices from one or more delivery devices. For example, a core wire with an electrolytically detachable junction can be used to separate the electrode device from the core wire. Pusher rods with mechanically detachable junctions are also contemplated.

21 Claims, 12 Drawing Sheets

(56) References Cited

OTHER PUBLICATIONS

PCT Written Opinion of the International Search Authority for PCT/US04/004680, Applicant: Scimed Life Systems, Inc., Forms PCT/ISA/237, dated Jul. 7, 2004 (5 pages).

PCT International Preliminary Report on Patentability (Chapter I of the Patent Cooperation Treaty) for PCT/US2004/004680, Applicant: Scimed Life Systems, Inc., Form PCT/IB/326 and 373, dated Sep. 16, 2005 (6 pages).

* cited by examiner

METHOD FOR INDIRECTLY ABLATING TISSUE USING IMPLANTED ELECTRODE DEVICES

RELATED APPLICATION DATA

This application is a continuation of U.S. patent application Ser. No. 11/258,417, filed on Oct. 24, 2005, now issued as U.S. Pat. No. 7,749,219, which itself is a continuation of U.S. patent application Ser. No. 10/387,892, filed Mar. 13, 2003, now issued at U.S. Pat. No. 6,979,330, the entire disclosures of which are expressly incorporated by reference herein. Priority is claimed pursuant to 35 U.S.C. §120.

FIELD OF THE INVENTION

The field of the invention relates generally to the structure and use of radio frequency (RF) electrosurgical probes for the treatment of solid tissue, and more particularly, to electrosurgical probes having multiple tissue-penetrating electrodes that are deployed in an array to treat large volumes of tissue.

BACKGROUND OF THE INVENTION

The delivery of radio frequency (RF) energy to target regions within solid tissue is known for a variety of purposes of particular interest to the present inventions. In one particular application, RF energy may be delivered to diseased regions (e.g., tumors) in target tissue for the purpose of tissue necrosis. RF ablation of tumors is currently performed within one of two core technologies.

The first technology uses a single needle electrode, which when attached to a RF generator, emits RF energy from the exposed, uninsulated portion of the electrode. This energy translates into ion agitation, which is converted into heat and induces cellular death via coagulation necrosis. The second technology utilizes multiple needle electrodes, which have been designed for the treatment and necrosis of tumors in the liver and other solid tissues. PCT application WO 96/29946 and U.S. Pat. No. 6,379,353 disclose such probes. In U.S. Pat. No. 6,379,353, a probe system comprises a cannula having a needle electrode array reciprocatably mounted therein. The individual electrodes within the array have spring memory, so that they assume a radially outward, arcuate configuration as they are advanced distally from the cannula.

When ablating lesions that are larger than the capability of the above-mentioned devices, the common practice is to stack ablations (i.e., perform multiple ablations) within a given area. This requires multiple electrode placements and ablations facilitated by the use of ultrasound imaging to visualize the electrode in relation to the target tissue. Because of the echogenic cloud created by the ablated tissue, however, this process often becomes difficult to accurately perform. This considerably increases treatment duration and requires significant skill for meticulous precision of multiple electrode placement.

Thus, there is a need for an improved system and method for ablating tissue regions that are larger than the single ablation capability of the electrode or electrode array being used.

SUMMARY OF THE INVENTION

In accordance with the present inventions, medical probe assemblies, tissue ablation kits, and tissue ablation methods contemplate the use of implanting multiple electrode devices into a treatment tissue region and ablating the tissue with a separate electrode device.

In accordance with a first aspect of the present inventions, a medical probe assembly comprises a single, or even multiple, needle electrode arrays, and an electrode delivery assembly configured for implanting the electrode array(s) into tissue. By way of non-limiting example, the electrode array(s) may be detachably coupled to the delivery assembly. The electrode array(s) may also evert proximally when introduced into the tissue to maximize its ablative capability. If multiple electrode arrays are contemplated, the delivery assembly can be configured to conveniently delivery them sequentially into the tissue.

In a preferred embodiment, the delivery assembly comprises an elongate tubular member, such as, e.g., a cannula, and a delivery device disposed within a lumen of the cannula, wherein the electrode array(s) are detachably coupled to the delivery device. The delivery device may be variously configured to detach the electrode array(s) therefrom. For example, the delivery device can comprise a core wire that includes one or more electrolytically detachable junctions coupled to the electrode array(s). As another example, the delivery device can comprise a pusher rod that includes one or more mechanically detachable junctions coupled to the electrode array(s).

In accordance with a second aspect of the present inventions, a tissue ablation kit comprises a plurality of needle electrode arrays configured for being implanted into tissue, and an ablation probe, such as, e.g., an electrosurgical probe, having one or more distally located electrodes configured for indirectly conveying radio frequency (RF) energy to the implanted electrode arrays.

In a preferred embodiment, the tissue ablation kit may further comprise an electrode delivery assembly configured for delivering the needle electrode arrays into the tissue. In this case, the needle electrode arrays may be detachably coupled to the delivery assembly. By way of non-limiting example, the delivery assembly can include an elongated tubular member, such as, e.g., a cannula, and one or more delivery devices configured to be slidably disposed within the lumen of the tubular member, wherein the needle electrode arrays are detachably coupled to the one or more delivery devices. If a single delivery device is used, it can be configured for sequentially delivering the needle electrode arrays into the tissue. If a plurality of delivery devices are used, each delivery device one can be configured to deliver a single electrode array. As previously described, the delivery device may be variously configured to detach the electrode array(s) therefrom, e.g., using one or more electrolytically or mechanically detachable junctions.

The ablation device may be configured to be slidingly coupled within the tubular member used to deliver the electrode arrays, or alternatively can be slidingly coupled within a separate tubular member. The one or more distally located ablation electrodes can include a single electrode or a plurality of electrodes, e.g., a plurality of needle electrodes arranged in an array.

In accordance with a third aspect of the present inventions, a method of ablating tissue (such as, e.g., a tumor) comprises implanting a plurality of electrode elements throughout the tissue, and simultaneously exposing the plurality of electrode elements to radio frequency (RF) energy to ablate the tissue adjacent the electrode elements, wherein at least one of the plurality of electrode elements is indirectly or directly exposed to RF energy. Indirect exposure of RF energy can be accomplished, e.g., by conveying RF energy from a separate RF electrode, which can be adjacent to or within the tissue, to the implanted electrode elements via tissue conductance and/ or inductance. Direct exposure of RF energy can be accomplished, e.g., by directly contacting the implanted electrode elements with a separate RF energy and conveying RF energy from the separate RF electrode to the implanted electrode elements. Although the present inventions should not be so limited in its broadest aspects, all of the electrode elements are preferably exposed to the RF energy. The electrode elements can take on any form, but in the preferred method, needle electrode arrays are used. In a preferred method, the electrode implantation comprises delivering the plurality of electrode elements within the tissue using a single or multiple delivery devices, and detaching the plurality of electrode elements from the delivery device(s). Although the present inventions should not be so limited in its broadest aspects, the indirect application of RF energy to the multiple implanted electrode devices distributed throughout the tissue, allows a greater region to be ablated than what would be ablated with just the electrosurgical probe. In addition, the implanted electrode devices provide an additional advantage of creating a roadmap to allow the progress of managing the ablated tissue (e.g., destruction or growth of a tumor) to be tracked during future follow-ups.

BRIEF DESCRIPTION OF THE DRAWINGS

The drawings illustrate the design and utility of preferred embodiments of the present invention, in which similar elements are referred to by common reference numerals. In order to better appreciate how the above-recited and other advantages and objects of the present inventions are obtained, a more particular description of the present inventions briefly described above will be rendered by reference to specific embodiments thereof, which are illustrated in the accompanying drawings. Understanding that these drawings depict only typical embodiments of the invention and are not therefore to be considered limiting of its scope, the invention will be described and explained with additional specificity and detail through the use of the accompanying drawings in which.

DETAILED DESCRIPTION OF THE PREFERRED EMBODIMENTS

Figure 1:
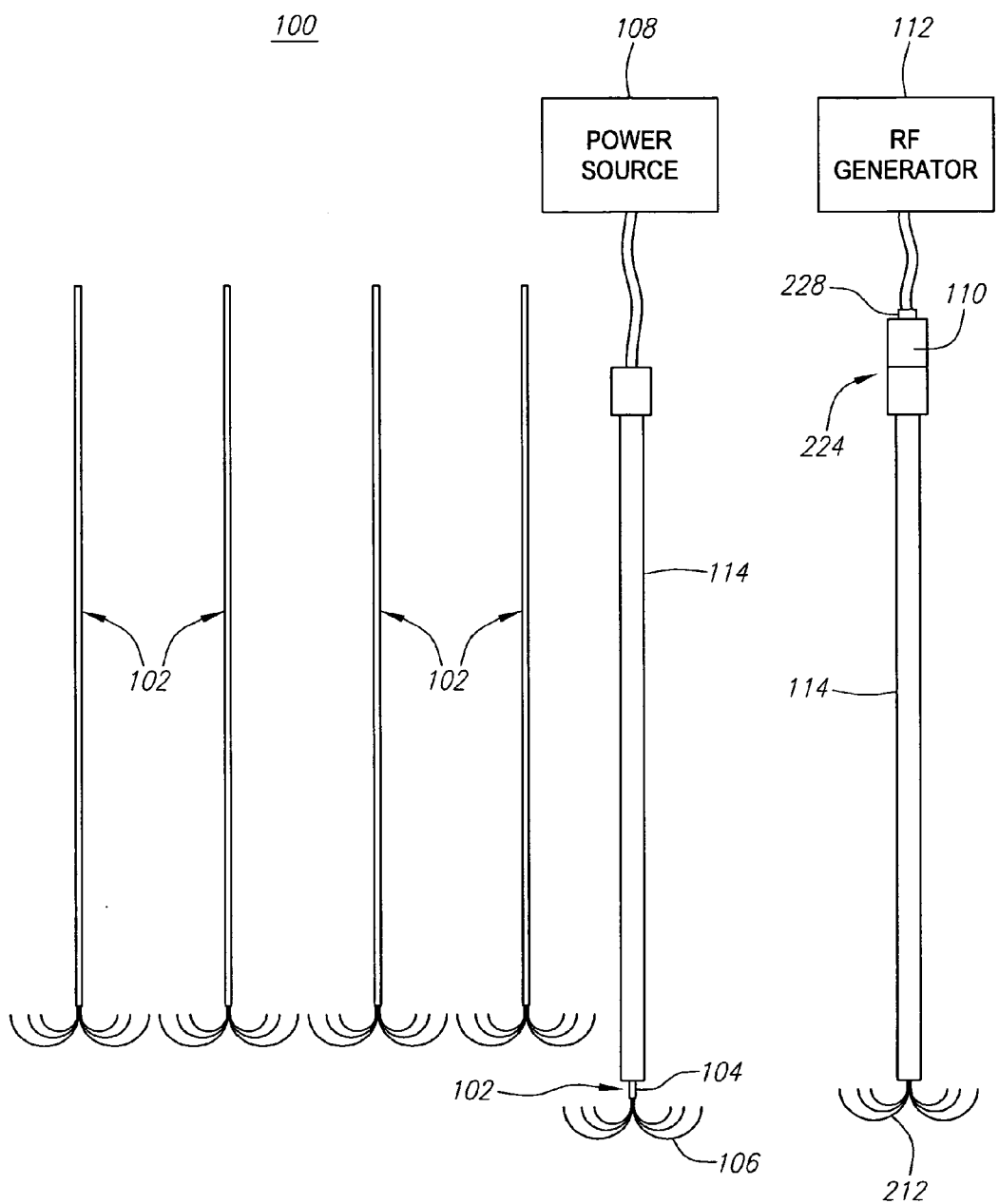
FIG. 1 is a plan view of tissue ablation system constructed in accordance with a preferred embodiment of the present inventions.

FIG. 1 illustrates a tissue ablation system 100 constructed in accordance with a preferred embodiment of the present inventions. The tissue ablation system 100 generally comprises a plurality of self-delivering single electrode assemblies 102, each of which includes a delivery device 104 and a distally mounted electrode device 106. Each of the delivery devices 104 is configured for detaching from, and implanting, the associated electrode device 106 within tissue. The tissue ablation system 100 further comprises a power source 108 that is configured for conveying electrical current through each of the single electrode assemblies 102 to detach the corresponding electrode device 106 from the delivery device 102 in a controlled manner. The tissue ablation system 100 further comprises an elongated cannula 114 configured for delivering the single electrode assemblies 102 to the tissue.

Thus, it can be appreciated that the delivery devices 104 can be exchanged within the cannula 114 to form an electrode delivery assembly 118 (shown in FIGS. 3 and 4) for the purposes of sequentially implanting the distally located electrode devices 106 into the tissue. Optional tubular members (not shown) can be provided with each single electrode assembly 102 to facilitate these exchanges.

The tissue ablation system 100 further comprises an electrosurgical probe 110 configured for indirectly delivering RF energy to the implanted electrode devices 106 to ablate the tissue, and a radio frequency (RF) generator 112 configured for supplying RF energy to the electrosurgical probe 110 in a controlled manner. As will be described in further detail below, this ablation process, as well as the following treatment management process, is facilitated by the implanted electrode elements 106. The previously described cannula 114 is configured for delivering the electrosurgical probe 110 to the tissue. Alternatively, separate cannulae can be used to deliver the single electrode assemblies 102 and electrosurgical probe 110.

The electrode devices 106 can be offered in various sizes or shapes to meet the needs of the specific situation. Usually, the cannula 114, single electrode assemblies 102, and electrosurgical probes 110 will be packaged and/or assembled together in a single sterile package and intended to be used together. Frequently, the cannula 114, single electrode assemblies 102, and electrosurgical probe 110 will be disposable. Alternatively, any or all of the components of the assembly may be sterilizable and reusable, at least for a limited number of uses. Thus, when referred to as a system, it is contemplated that the components of the system may be made available separately and later combined by a user into a single system.

Figure 2:
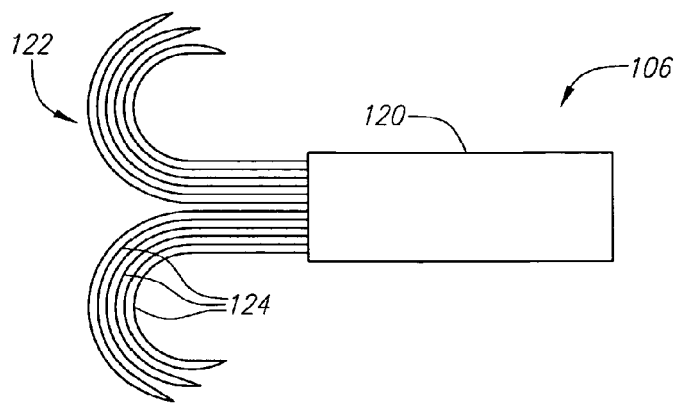
FIG. 2 is a plan view of an electrode device used with the tissue ablation system of FIG. 1.

Referring now to FIG. 2, the electrode device 106 comprises a cylindrical connector member 120 and a needle electrode array 122 mounted to the distal end of the connector member 120. The electrode array 122 comprises a plurality of tissue penetrating needle electrodes 124 that are suitably coupled to the connector member 120 by, e.g., welding. Each of the individual needle electrodes 124 is in the form of a small diameter metal element, which can penetrate into tissue as it is advanced from a target site within the target region. When deployed from the cannula 114, the needle electrode array 122 is placed in a three-dimensional configuration that usually defines a generally cylindrical, conical, or spherical volume having a periphery with a maximum radius in the range from 0.5 to 3 cm.

The needle electrodes 124 are resilient and pre-shaped to assume a desired configuration when advanced into tissue. In the illustrated embodiment, the needle electrodes 124 diverge radially outwardly from the cannula 114 in a uniform pattern, i.e., with the spacing between adjacent needle electrodes 124 diverging in a substantially uniform and/or symmetric pattern. In the illustrated embodiment, the needle electrodes 124 also evert proximally, so that they face partially or fully in the proximal direction when fully deployed. In exemplary embodiments, pairs of adjacent needle electrodes 124 can be spaced from each other in similar or identical, repeated patterns and can be symmetrically positioned about an axis of the connector member 120. It will be appreciated that a wide variety of particular patterns can be provided to uniformly cover the region to be treated. It should be noted that a total of six needle electrodes 124 are illustrated in FIG. 1. Additional needle electrodes 124 can be added in the spaces between the illustrated electrodes 124, with the maximum number of needle electrodes 124 determined by the electrode width and total circumferential distance available (i.e., the needle electrodes 124 could be tightly packed).

Each individual needle electrode 124 is preferably composed of a single wire that is formed from resilient conductive metals having a suitable shape memory, such as stainless steel, nickel-titanium alloys, nickel-chromium alloys, spring steel alloys, and the like. The wires may have circular or non-circular cross-sections, but preferably have rectilinear cross-sections. In this manner, the needle electrodes 124 are generally stiffer in the transverse direction and more flexible in the radial direction. By increasing transverse stiffness, proper circumferential alignment of the needle electrodes 124 within the cannula 114 is enhanced. Exemplary needle electrodes will have a width (in the circumferential direction) in the range from 0.2 mm to 0.6 mm, preferably from 0.35 mm to 0.40 mm, and a thickness (in the radial direction) in the range from 0.05 mm to 0.3 mm, preferably from 0.1 mm to 0.2 mm. The cylindrical connector member 120 may be composed of the same materials as the needle electrodes 124.

The distal ends of the needle electrodes 124 may be honed or sharpened to facilitate their ability to penetrate tissue. The distal ends of these needle electrodes 124 may be hardened using conventional heat treatment or other metallurgical processes. They may be partially covered with insulation, although they will be at least partially free from insulation over their distal portions. Optionally, the needle electrodes 124 can be coated with a therapeutic agent, e.g., a drug, chemical, or radioactive agent.

Figure 3:
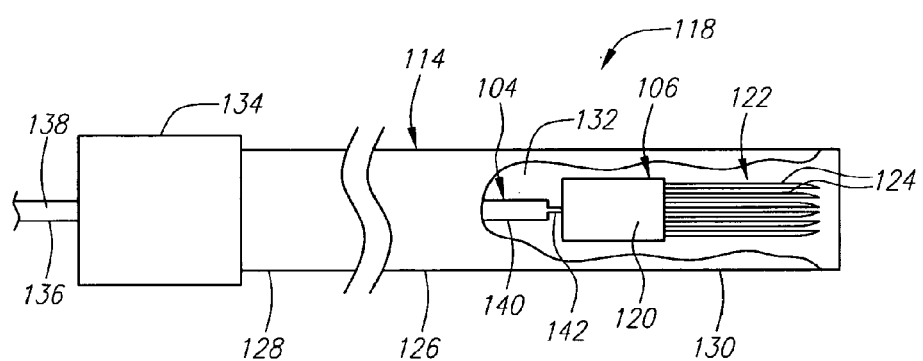
FIG. 3 is a partially cutaway view of a preferred embodiment of a single electrode delivery assembly used in the tissue ablation system of FIG. 1 to deliver the electrode device to tissue via an electrolytically detachable junction, wherein the electrode device is particularly shown retracted within a cannula.
Figure 4:
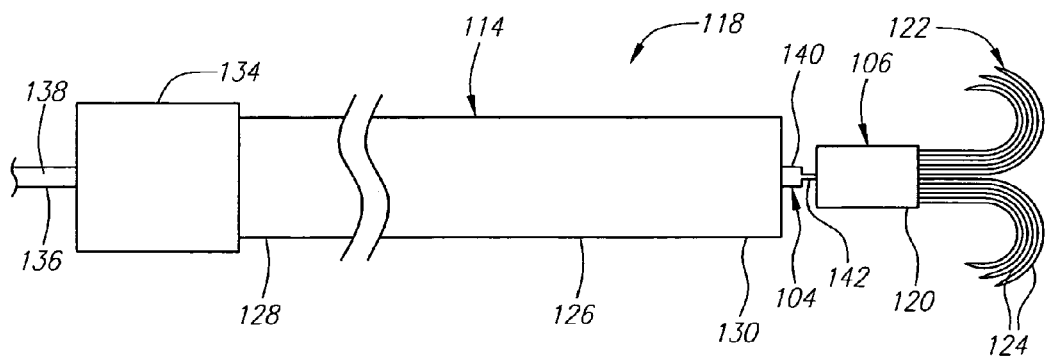
FIG. 4 is a partially cut-away view of the single electrode delivery assembly of FIG. 3, wherein the electrode device is particularly shown deployed from the cannula.

Referring specifically now to FIGS. 3 and 4, the electrode delivery assembly 118 generally comprises the previously described cannula 114 and delivery device 104, which is slidably disposed within the cannula 114. As previously noted, one of the electrode devices 106 is detachably coupled to the delivery device 104. It can be appreciated that longitudinal translation of the delivery device 104 relative to the cannula 114 in the distal direction deploys the electrode array 122 of the electrode device 106 from a radially collapsed configuration (FIG. 3) out of the distal end 130 of the cannula 114 into a deployed configuration (FIG. 4).

The cannula 114 comprises a tubular shaft 126 having a proximal end 128, a distal end 130, and a central lumen 132 extending through the cannula shaft 126 between the proximal end 128 and the distal end 130. As will be described in further detail below, the cannula shaft 126 may be rigid, semi-rigid, or flexible depending upon the designed means for introducing the cannula 114 to the target tissue. The cannula shaft 126 is composed of a suitable material, such as plastic, metal or the like, and has a suitable length, typically in the range from 5 cm to 30 cm, preferably from 10 cm to 20 cm. The cannula shaft 126 has an outside diameter consistent with its intended use, typically being from 1 mm to 5 mm, usually from 1.3 mm to 4 mm. The cannula shaft 126 has an inner diameter in the range from 0.7 mm to 4 mm, preferably from 1 mm to 3.5 mm. The cannula 114 further comprises a connector sleeve 134 is mounted to the proximal end 128 of the cannula shaft 126 for ease of handling.

The delivery device 104 comprises a core wire 136 that includes a proximal end 138 to which a power supply (not shown) is coupled, and a distal end 140 to which the electrode device 106, and specifically the connector member 120, is coupled, e.g., by welding. The core wire 136 is composed of a suitable electrically conductive and biocompatible material, such as, e.g., stainless steel. The delivery device 104 further comprises an electrolytically detachable junction 142 disposed on the distal end 140 of the core wire 136 proximally adjacent to the electrode device 106. Thus, the connector member 120 of the electrode device 106 is detachably coupled to the core wire 136, so that the electrode device 106, including the electrode array 122, will separate from the core wire 136 when the junction 142 is severed. In the illustrated embodiment, the detachable junction 142 is shown disposed on the distal tip of the core wire 136, but can also be located proximal to the distal tip, such that a portion of the core wire 136 will become separated with the electrode device 106 from the remainder of the core wire 136.

The electrolytically detachable junction 142 provides a controlled manner in which the electrode device 106 can be detached from the core wire 136. Specifically, the detachable junction 142 is more susceptible to electrolysis in an ionic solution, such as blood and other body fluids, than is the core wire 136 and electrode device 106. Thus, when an electrical current is applied to the core wire 136, the electrolytically detachable junction 142 is configured to disintegrate in the presence of the ionic fluid. To this end, the core wire 136 is electrically coupled to one pole of a power supply (not shown), and a patch (also not shown) is electrically coupled to the other pole of the power supply. The patch is placed on skin of the patient to complete the circuit from the power supply, through the core wire 136, through the detachable junction 142, through the ionic solution in the tissue, through the patch, and back to the power supply. Other return routes may be used as the designer sees fit.

The delivery device 104 further comprises an insulative layer (not shown) that covers core wire 136 from a point just proximal to the detachable junction 142 back to a point near the proximal end 138 of the core wire 136, which is left bare for proper connection to the power supply. In this manner, the electrolysis process is more focused on the detachable junction 142. The insulative layer is composed of a suitable material, such as, e.g., polytetrafluoroethylene (e.g., Teflon®), polyparaxylylene (e.g., Parylene), polyethyleneterephthalate (PET), polybutyleneterephthalate (PBT), cyanoacrylate adhesives, or other suitable insulating material. Further details regarding the structure on operation of delivery devices that utilize electrolytically detachable junction to deploy implants within tissue is described in U.S. Pat. No. 5,984,929, entitled "Fast Detaching Electronically Isolated Implant," which is hereby fully and expressly incorporated herein by reference.

Figure 5:
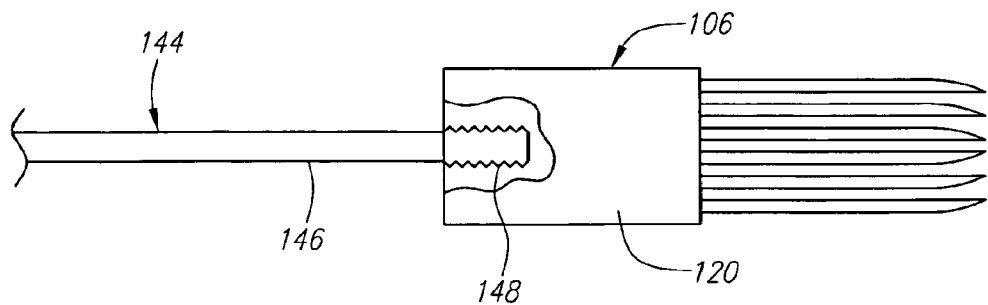
FIG. 5 is a partially cutaway view of an alternative preferred embodiment of a single electrode delivery assembly used in the tissue ablation system of FIG. 1 to deliver the electrode device to tissue via one type of a mechanically detachable junction.

Electrolytic detachment is not the only manner of delivering the electrode device to the tissue. For example, FIG. 5 shows a delivery device 144 that utilizes a mechanical detachment means for delivering the electrode device 106 to the tissue. In this configuration, delivery device 104 includes a pusher rod 146 that is coupled to the electrode device 106 via a mechanical detachable junction, and specifically, a threaded arrangement 148 between the distal end of the pusher rod 146 and the connector member 120 of the electrode device 106. Thus, it can be appreciated that the electrode device 106 can be separated from the delivery device 104 by unscrewing the pusher rod 146 from the connector member 120.

Figure 6:
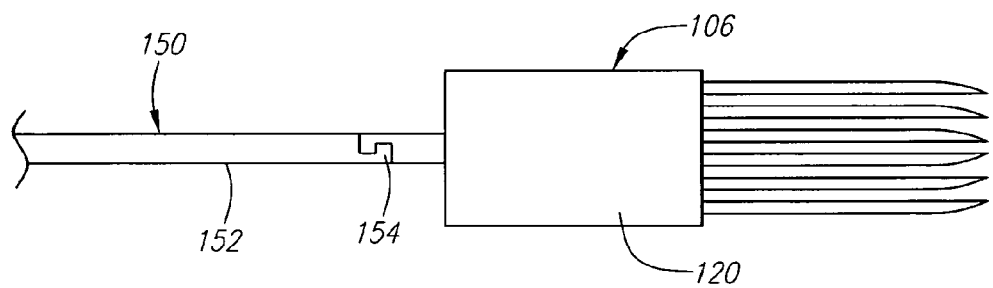
FIG. 6 is a partially cutaway view of another alternative preferred embodiment of a single electrode delivery assembly used in the tissue ablation system of FIG. 1 to deliver the electrode device to tissue via another type of a mechanically detachable junction.

FIG. 6 shows a delivery device 150 that utilizes another mechanical detachment means for delivering the electrode device 106 to the tissue. In this configuration, the delivery device 104 includes a pusher rod 152 that is coupled to the electrode device 106 via a mechanical detachable junction, and specifically, interlocking clasps 154 that are mounted on the distal end of the pusher rod 152 and the proximal end of the connector member 120 of the electrode device 106. Thus, it can be appreciated that the electrode device 106 can be separated from the delivery device 104 by merely pushing the electrode device 106 out from the distal end 130 of the cannula 114 to separate the interlocking clasps 154.

Figure 7:
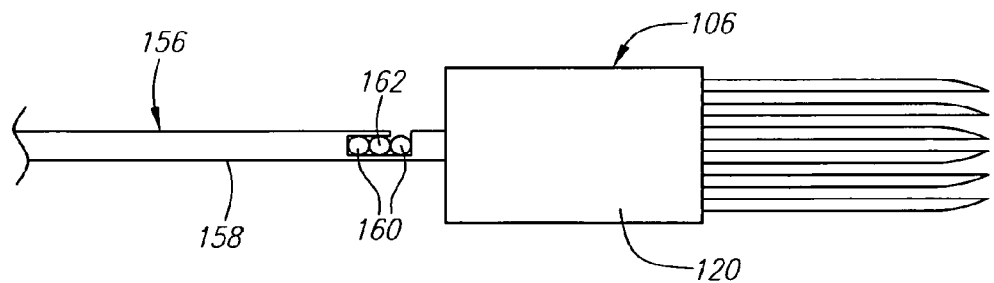
FIG. 7 is a partially cutaway view of still another alternative preferred embodiment of a single electrode delivery assembly used in the tissue ablation system of FIG. 1 to deliver the electrode device to tissue via still another type of a mechanically detachable junction.

FIG. 7 shows a delivery device 156 that utilizes still another mechanical detachment means for delivering the electrode device 106 to the tissue. In this configuration, the delivery device 104 includes a pusher rod 158 that is coupled to the electrode device 106 via a mechanical detachable junction, and specifically, spherical elements 160/162 that are mounted to the distal end of the pusher rod 158 and the proximal end of the connector member 120 of the electrode device 106. In this embodiment, two axially spherical elements 160 are mounted to the proximal end of the connector member 120, and one spherical element 162 is mounted to the distal end of the pusher rod 158. As illustrated, the single spherical element 162 associated with the pusher rod 158 resides between the pair of axially spaced spherical elements 160 associated with the connector member 120. Thus, it can be appreciated that the electrode device 106 can be separated from the delivery device 104 by merely pushing the electrode device 106 out from the distal end 130 of the cannula 114 to separate the single spherical element 162 from the pair of spherical elements 160.

Figure 8:
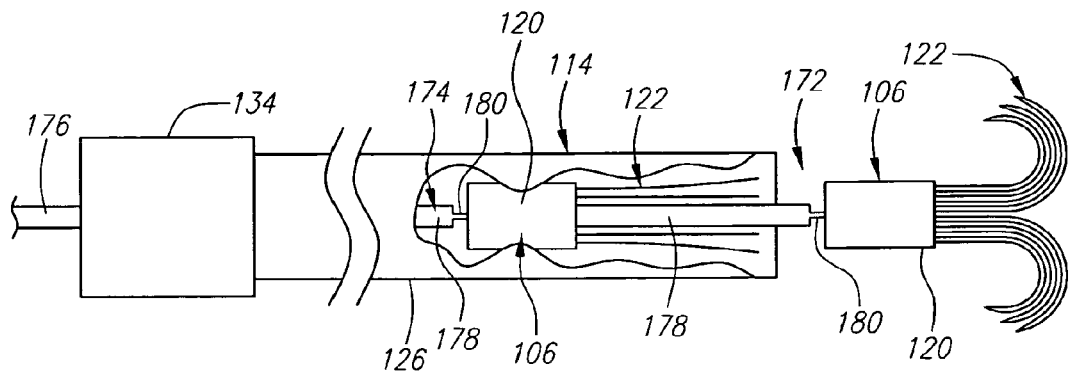
FIG. 8 is a partially cutaway view of a preferred embodiment of a multiple electrode delivery assembly used in the tissue ablation system of FIG. 1 to sequentially deliver multiple electrode devices to tissue via a series of electrolytically detachable junctions.

Each of the previously described delivery devices is designed to deliver a single electrode device 106 into the tissue. It should be noted, however, that delivery devices can be designed to deliver multiple electrode devices 106 into the tissue. For example, FIG. 8 illustrates a self-delivering multiple electrode assembly 172 comprising a delivery device 174 and a plurality of the previously described electrode devices 106. The delivery device 174 comprises a core wire 176 formed of core wire segments 178 between the respective electrode devices 106. The core wire 176 is composed of the same material as the previously described core wire 136. As illustrated, the multiple electrode devices 106 are disposed along the length of the core wire 136. The delivery device 104 also comprises multiple electrolytic detachable junctions 180 disposed along the length of the core wire 136 between the electrode devices 106. The delivery device 104 further comprises an insulative layer (not shown) that covers the core wire 136 between the detachable junctions 178 to focus the electrolysis process on the detachable junctions 180. Thus, it can be appreciated that the multiple electrode devices 106 can be separated from the delivery device 104 by sequentially deploying the electrode devices 106 from the cannula 114 and conveying electrical energy through the core wire 136 to disintegrate the detachable junction 180 that is presently exposed to the electrolytic fluids. Notably, any portion of the core wire 136 distal to the immediately detached electrode device 106 will accordingly be detached with the electrode device 106 and may facilitate penetration of the electrode device 106 through the tissue.

Figure 9:
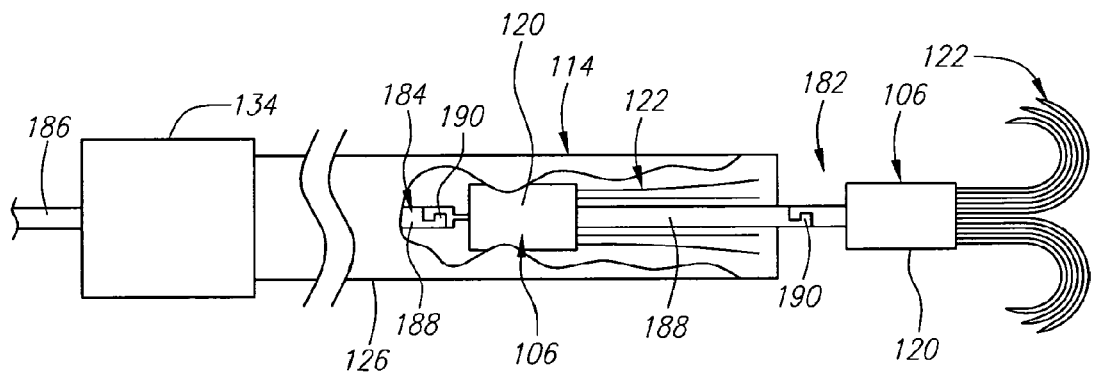
FIG. 9 is a partially cutaway view of another preferred embodiment of a multiple electrode delivery assembly used in the tissue ablation system of FIG. 1 to sequentially deliver multiple electrode devices to tissue via a series of one type of mechanically detachable junctions.

This multiple electrode delivery configuration can also be applied to mechanical detachment means. For example, FIG. 9 illustrates a self-delivering multiple electrode assembly 182 comprising a delivery device 184 and a plurality of the previously described electrode devices 106. The delivery device 184 comprises a pusher rod 186 formed of rod segments 188 between the respective electrode devices 106. The delivery device 184 further comprises multiple mechanical junctions, and specifically, interlocking clasps 190 disposed on the proximal ends of the connector members 120 of the electrode devices 106 and the distal ends of the pusher rod segments 188. Thus, it can be appreciated that the multiple electrode devices 106 can be separated from the delivery device 184 by merely sequentially pushing the electrode devices 106 out from the distal end 130 of the cannula 114 to separate each of the interlocking clasps 190 as they exit the cannula 114. Notably, any portion of the pusher rod segment 188 distal to the immediately detached electrode device 106 will accordingly be detached with the electrode device 106 and may facilitate penetration of the electrode device 106 through the tissue.

Figure 10:
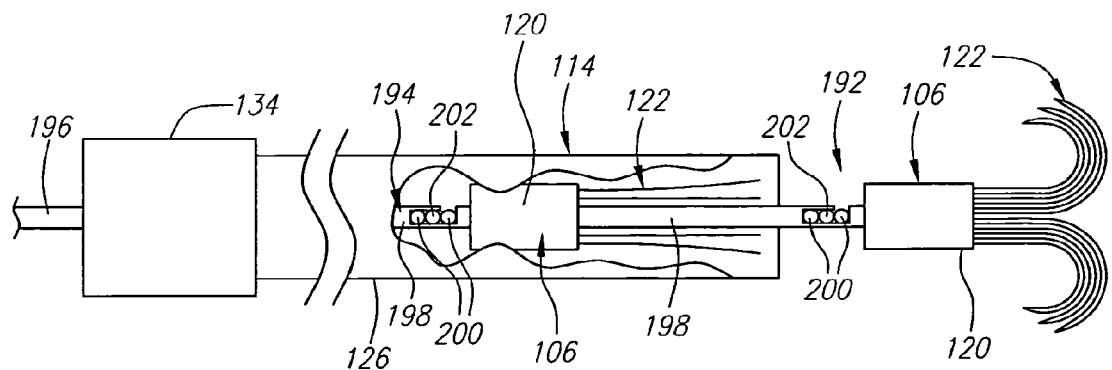
FIG. 10 is a partially cutaway view of another preferred embodiment of a multiple electrode delivery assembly used in the tissue ablation system of FIG. 1 to sequentially deliver multiple electrode devices to tissue via a series of another type of mechanically detachable junctions.

As another example, FIG. 10 illustrates a self-delivering multiple electrode assembly 192 comprising a delivery device 194 and a plurality of the previously described electrode devices 106. The delivery device 194 comprises a pusher rod 196 formed of rod segments 198 between the respective electrode devices 106. The delivery device 104 further comprises multiple mechanical junctions, and specifically, pairs of axially spaced spherical elements 200 mounted to the proximal ends of the connector members 120 of the electrode devices 106, and single spherical elements 202 mounted to the distal ends of the rod segments 198 and residing within the spaces between the respective spherical elements pairs 200. Thus, it can be appreciated that the multiple electrode devices 106 can be separated from the delivery device 194 by merely sequentially pushing the electrode devices 106 out from the distal end 130 of the cannula 114 to separate each of the ball arrangements as they exit the cannula 114. Notably, any portion of the pusher rod segment 198 distal to the immediately detached electrode device 106 will accordingly be detached with the electrode device 106 and may facilitate penetration of the electrode device 106 through the tissue.

Figure 11:
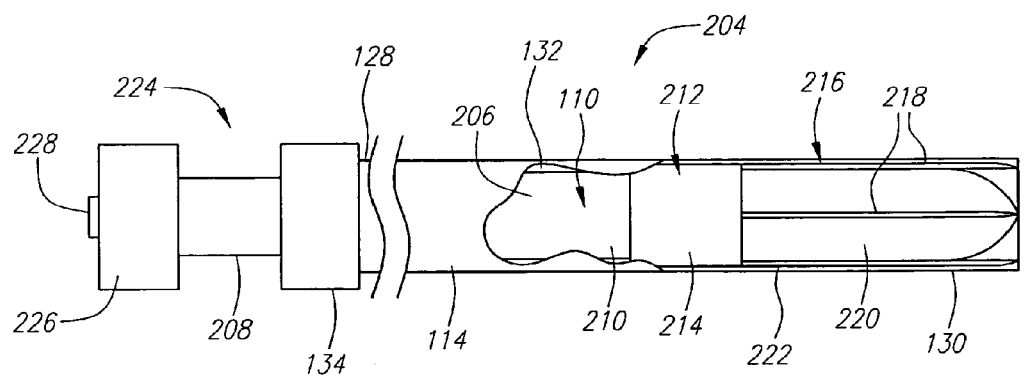
FIG. 11 is a partially cutaway view of a preferred embodiment of an electrosurgical probe assembly used in the tissue ablation system of FIG. 1 to ablate the tissue, wherein an electrode device is particularly shown retracted within a cannula.
Figure 12:
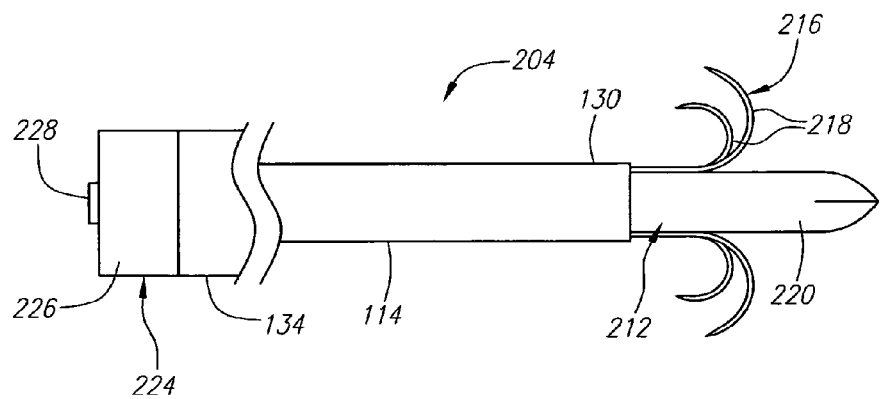
FIG. 12 is a partially cut-away view of the electrosurgical probe assembly of FIG. 11, wherein the electrode device is particularly shown deployed from the cannula.

Referring now to FIGS. 11 and 12, the electrosurgical probe 110 is configured to be slidably disposed within the central lumen 132 of the cannula 114 to form an electrosurgical probe assembly 204. Alternatively, a separate cannula can be used with the electrosurgical probe 110. The probe 110 comprises a reciprocating shaft 206 having a proximal end 208 and a distal end 210, and an electrode device 212 mounted to the distal end 210 of the shaft 206. Like the cannula 114, the shaft 206 is composed of a suitable material, such as plastic, metal or the like. The electrode device 212 is similar to the previously described electrode device 106 in that it includes a cylindrical connector member 214 and an array 216 of tissue penetrating needle electrodes 218 mounted thereto. Other types of electrode devices 212, however, are contemplated. It can be appreciated longitudinal translation of the shaft 206 relative to the cannula 114 in a distal direction deploys the electrode array 216 from the distal end 130 of the cannula 114 (FIG. 12), and longitudinal translation of the shaft 206 relative to the cannula 114 in a proximal direction retracts the electrode array 216 into the distal end 130 of the cannula 114 (FIG. 11).

The electrosurgical probe 110 further comprises a core member 220 mounted to the connector member 214 of the electrode device 212, and being disposed coaxially within the central lumen 132 of the cannula 114 to maintain substantially equal circumferential spacing between the needle electrodes 124 retracted in the central lumen 132. An annular envelope 222 is defined between the inner surface of the cannula 114 and the outer surface of the core member 220 when the core member 220 is retracted within the distal end 130 of the cannula 114. The width of the annular envelope 222 (defined by the distance between the outer surface of the core member 220 and the inner surface of the cannula 114) is typically in the range from 0.1 mm to 1 mm, preferably from 0.15 mm to 0.5 mm, and will usually be selected to be slightly larger than the thickness of the individual electrodes 124 in the radial direction.

In this manner, when retracted within the cannula 114 (FIG. 11), the electrode array 122 is placed in a radially collapsed configuration, and the individual needle electrodes 124 are constrained and held in generally axially aligned positions within the cannula 114 over the outer cylindrical surface of the core member 220, to facilitate its introduction to the tissue target site.

It will be appreciated that as the core member 220 distally moves with the electrode array 122, it will enter the tissue at the same time as the electrode array 122. To enhance tissue penetration, the core member 220 comprises a sharpened distal end. The proximal ends of the needle electrodes 218 may be directly coupled to the connector assembly, or alternatively, may be indirectly coupled thereto via other intermediate electrical conductors, e.g., RF wires. Optionally, the shaft 206 and any component between the shaft 206 and the needle electrodes 218, are composed of an electrically conductive material, such as stainless steel, and may therefore conveniently serve as intermediate electrical conductors.

In the illustrated embodiment, the RF current is delivered to the electrode array 216 in a monopolar fashion, which means that current will pass from the electrode array 216, which is configured to concentrate the energy flux in order to have an injurious effect on the surrounding tissue, and a dispersive electrode (not shown), which is located remotely from the electrode array 216 and has a sufficiently large area (typically 130 cm2 for an adult), so that the current density is low and non-injurious to surrounding tissue. In the illustrated embodiment, the dispersive electrode may be attached externally to the patient, e.g., using a contact pad placed on the patient's flank. In a monopolar arrangement, the needle electrodes 218 are bundled together with their proximal portions having only a single layer of insulation over the cannula 114.

Alternatively, the RF current is delivered to the electrode array 216 in a bipolar fashion, which means that current will pass between "positive" and "negative" electrodes 124 within the array 216. In a bipolar arrangement, the positive and negative needle electrodes 218 will be insulated from each other in any regions where they would or could be in contact with each other during the power delivery phase.

Optionally, the core member 220 may be electrically coupled to the electrode array 216, in which case it acts as an additional needle electrode of the same polarity as the electrodes 218, or may be electrically isolated from the electrodes 218. When the core member 220 is electrically isolated, it can remain neutral during a treatment protocol, or alternatively it may be energized in the opposite polarity, and thus acts as a return electrode in a bipolar arrangement.

The electrode surgical probe 110 may optionally include cooling features, so that the electrode array 216 remains relatively cool in the presence of RF energy, thereby providing for a more efficient and effective ablation procedure. For example, the electrode array 216 can be passively cooled by using a heat sink and a coolant conduit in fluid communication with the heat sink. Further details on this cooling feature is disclosed in copending application Ser. No. 10/387,812. Publication No. 2004-0181214, which is hereby fully and expressly incorporated herein by reference.

The probe assembly 204 further comprises a connector assembly 224, which includes the previously described connector sleeve 134 mounted to the proximal end 128 of the cannula 114, and a connector member 226 slidably engaged with the sleeve 134 and mounted to the proximal end 208 of the shaft 206. The connector member 214 comprises an electrical connector 228 in which the proximal ends of the needle electrodes 218 (or alternatively, intermediate conductors) extending through the shaft 206 of the probe 110 are coupled. The connector assembly 224 can be composed of any suitable rigid material, such as, e.g., metal, plastic, or the like.

Referring back to FIG. 1, the RF generator 112 is electrically connected to the electrical connector 228 of the connector assembly 224, which as previously described, is directly or indirectly electrically coupled to the electrode device 212. The RF generator 112 is a conventional RF power supply that operates at a frequency in the range from 200 kHz to 1.25 MHz, with a conventional sinusoidal or non-sinusoidal wave form. Such power supplies are available from many commercial suppliers, such as Valleylab, Aspen, and Bovie. Most general purpose electrosurgical power supplies, however, operate at higher voltages and powers than would normally be necessary or suitable for vessel occlusion. Thus, such power supplies would usually be operated at the lower ends of their voltage and power capabilities. More suitable power supplies will be capable of supplying an ablation current at a relatively low voltage, typically below 150V (peak-to-peak), usually being from 50V to 100V. The power will usually be from 50 W to 200 W, usually having a sine wave form, although other wave forms would also be acceptable. Power supplies capable of operating within these ranges are available from commercial vendors, such as Boston Scientific Corporation of San Jose, Calif., who markets these power supplies under the trademarks RF2000™ (100 W) and RF3000™ (200 W).

Further details regarding needle electrode array-type probe arrangements are disclosed in U.S. Pat. No. 6,379,353, entitled "Apparatus and Method for Treating Tissue with Multiple Electrodes," which is hereby expressly incorporated herein by reference.

Having described the structure of the tissue ablation system 100, its operation in treating targeted tissue will now be described. The treatment region may be located anywhere in the body where hyperthermic exposure may be beneficial. Most commonly, the treatment region will comprise a solid tumor within an organ of the body, such as the liver, kidney, pancreas, breast, prostrate (not accessed via the urethra), and the like. The volume to be treated will depend on the size of the tumor or other lesion, typically having a total volume from 1 cm3 to 150 cm3, and often from 2 cm3 to 35 cm3. The peripheral dimensions of the treatment region will usually be regular, e.g., spherical or ellipsoidal, but will more usually be irregular. The treatment region may be identified using conventional imaging techniques capable of elucidating a target tissue, e.g., tumor tissue, such as ultrasonic scanning, magnetic resonance imaging (MRI), computer-assisted tomography (CAT), fluoroscopy, nuclear scanning (using radiolabeled tumor-specific probes), and the like. Preferred is the use of high resolution ultrasound of the tumor or other lesion being treated, either intraoperatively or externally.

Figure 13A:
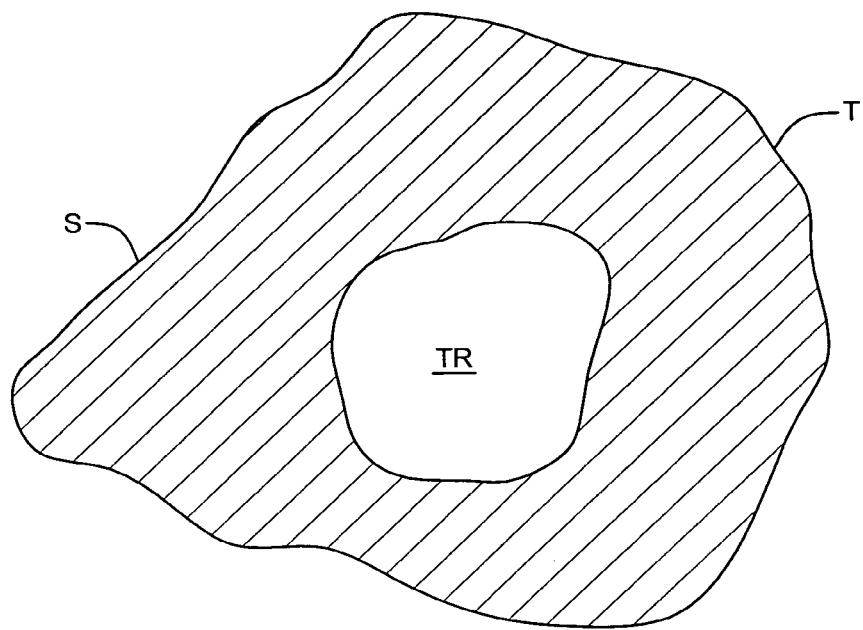
FIGS. 13A-13I illustrate cross-sectional views of one preferred method of using the tissue ablation system of FIG. 1 to treat tissue.
Figure 13B:
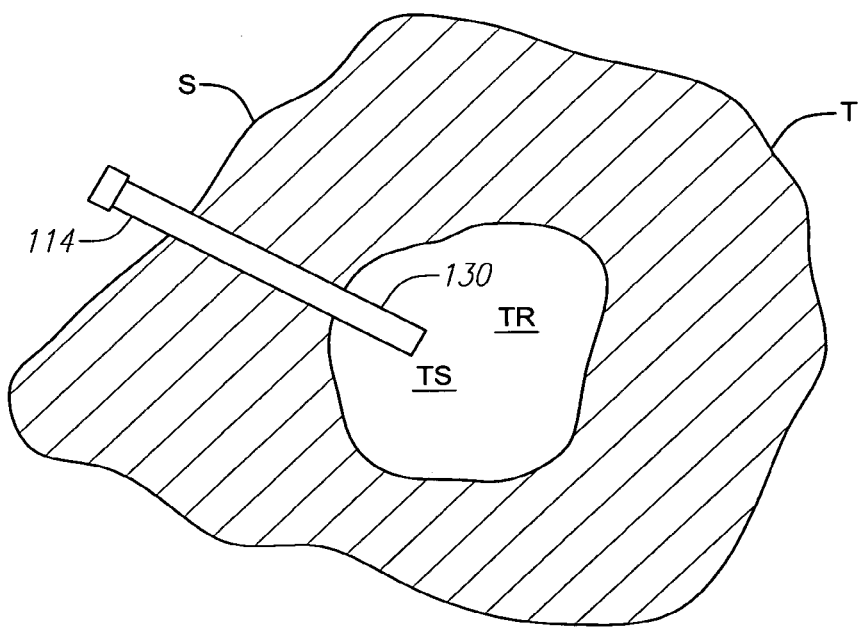

Referring now to FIGS. 13A-13I, the operation of the tissue ablation system 100 is described in treating a treatment region TR within a tissue located beneath the skin or an organ surface S of a patient. The tissue T prior to treatment is shown in FIG. 13A. The cannula 114 is first introduced within the treatment region TR, so that the distal end 130 of the cannula 114 is located at the target site TS, as shown in FIG. 13B. This can be accomplished using any one of a variety of techniques.

In some cases, the cannula 114 may be introduced to the target site TS percutaneously directly through the patient's skin or through an open surgical incision. In this case, the cannula 114 may have a sharpened tip, e.g., in the form of a needle, to facilitate introduction to the treatment region. In such cases, it is desirable that the cannula 114 or needle be sufficiently rigid, i.e., have a sufficient column strength, so that it can be accurately advanced through tissue. In other cases, the cannula 114 may be introduced using an internal stylet that is subsequently exchanged for the therapeutic components. In this latter case, the cannula 114 can be relatively flexible, since the initial column strength will be provided by the stylet. More alternatively, a component or element may be provided for introducing the cannula 114 to the treatment region. For example, a conventional sheath and sharpened obturator (stylet) assembly can be used to initially access the target site. The assembly can be positioned under ultrasonic or other conventional imaging, with the obturator/stylet then removed to leave an access lumen through the sheath. The cannula 114 can then be introduced through the sheath lumen, so that the distal end 130 of the cannula 114 advances from the sheath into the target site TS.

Figure 13C:
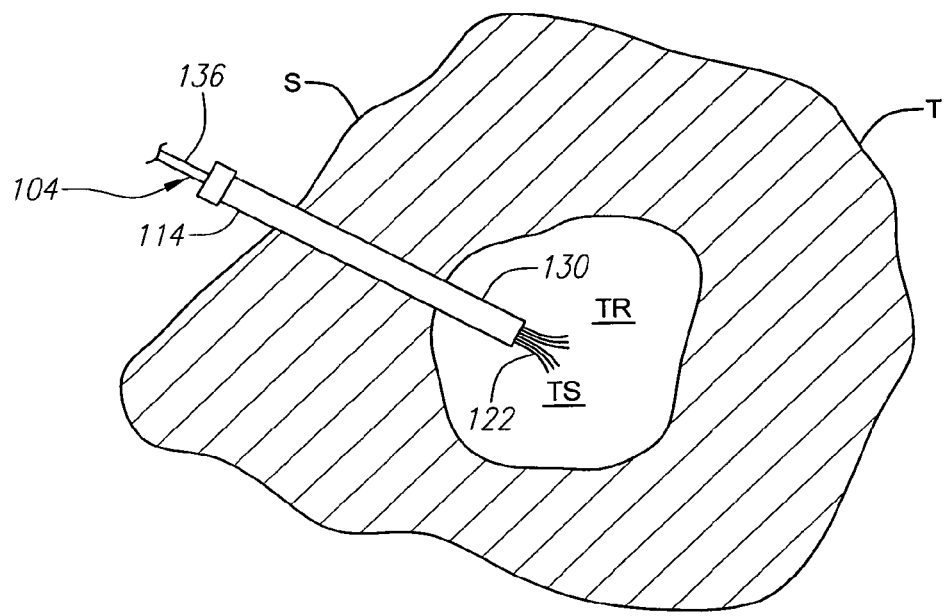
Figure 13D:
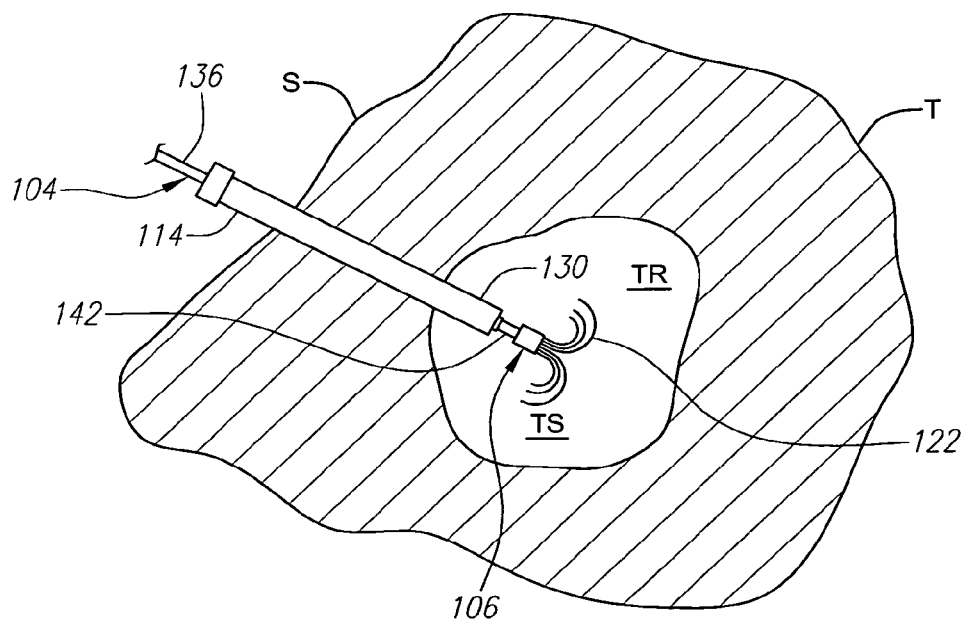
Figures 1, 13C:
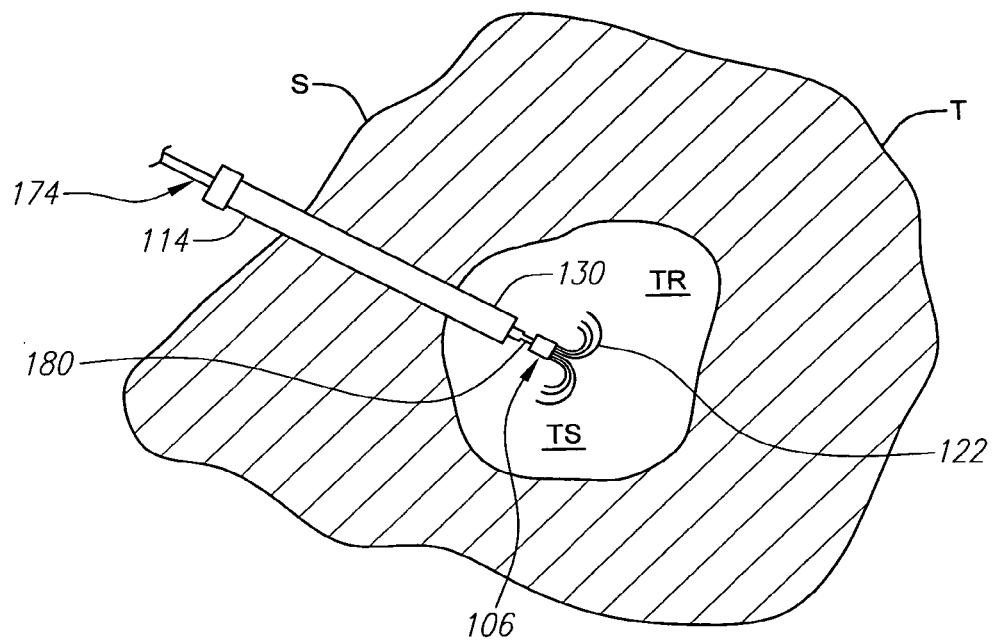
Figures 1, 13D:
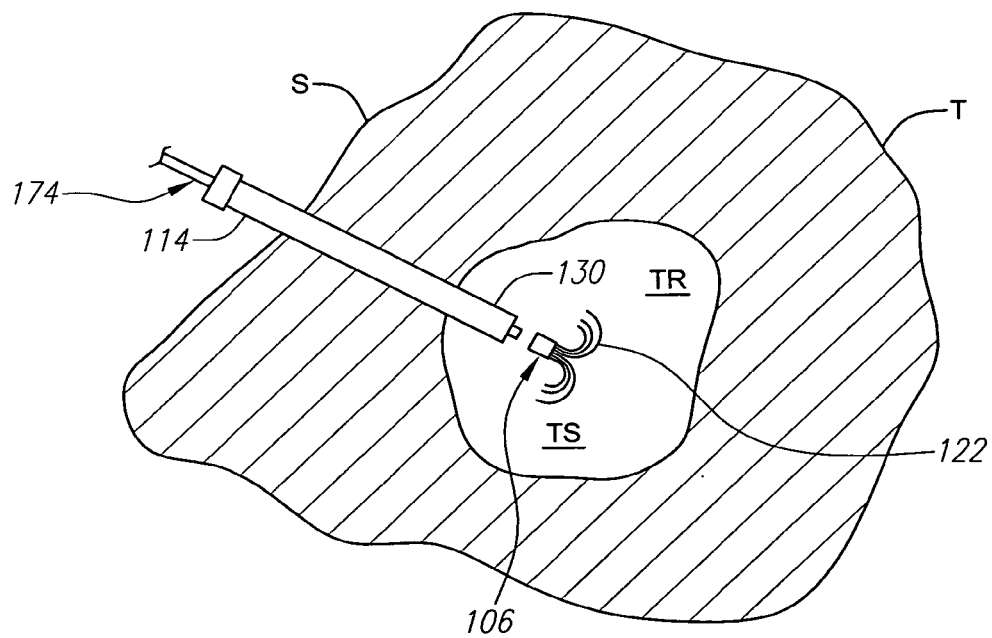
Figure 13E:
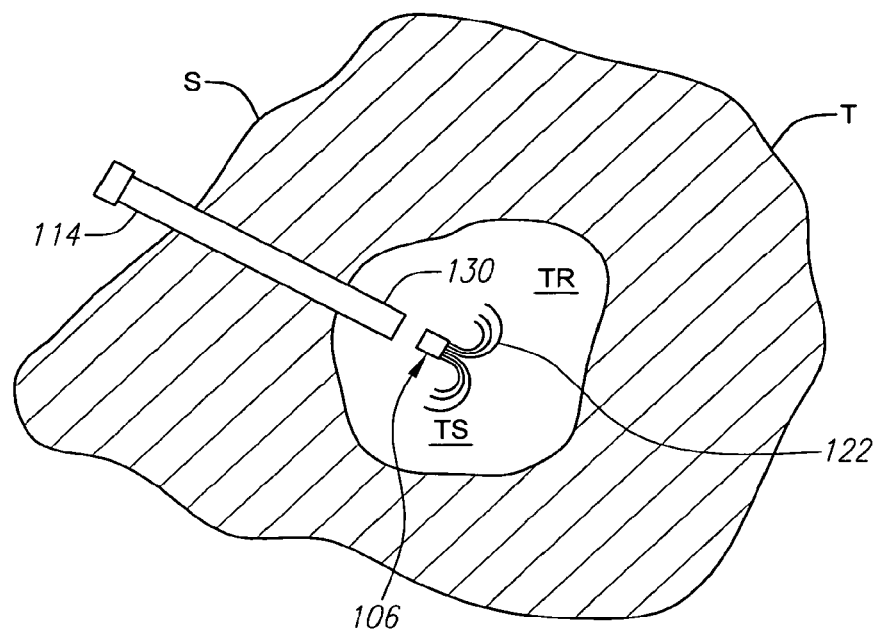
Figure 13F:
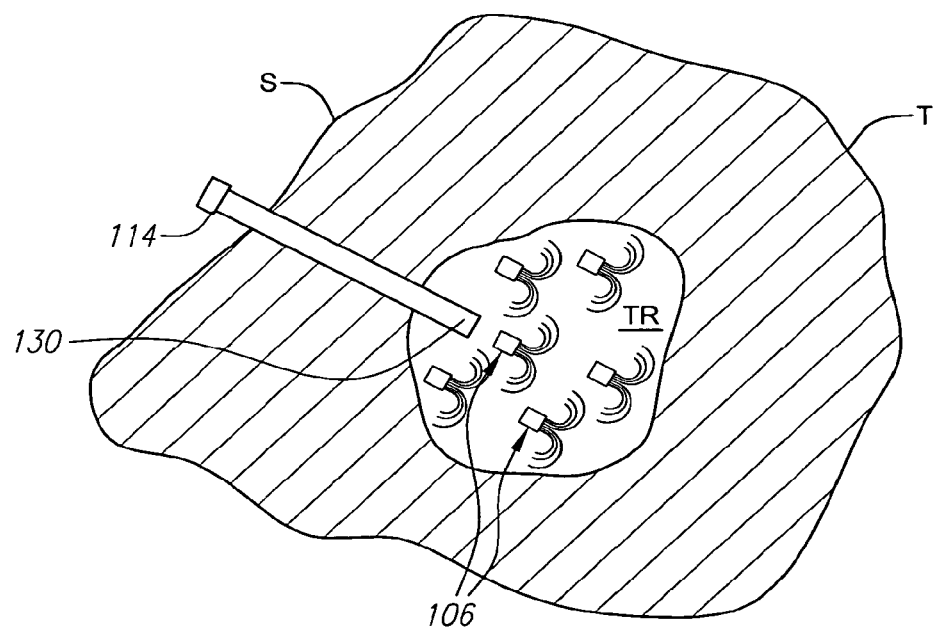
Figures 1, 13E:
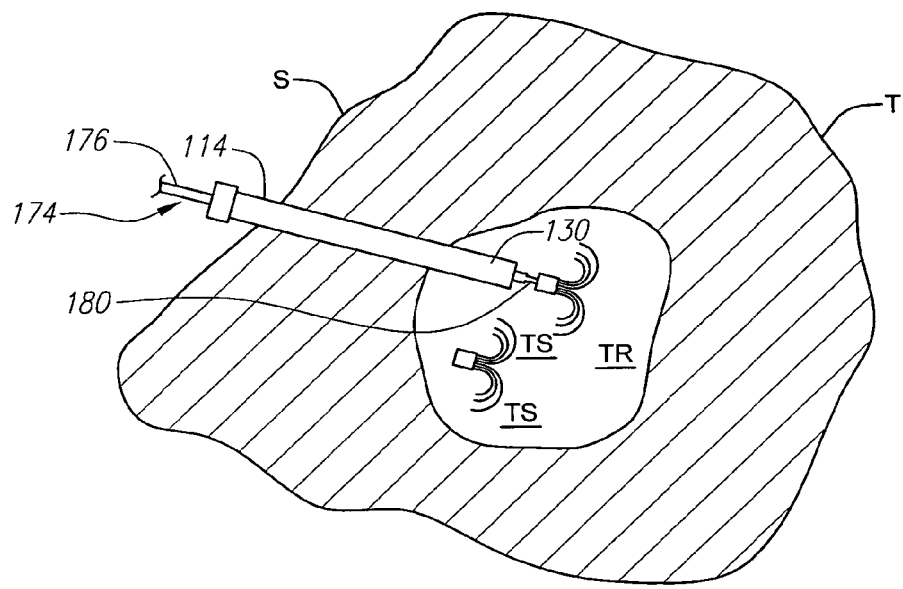
Figures 1, 13F:
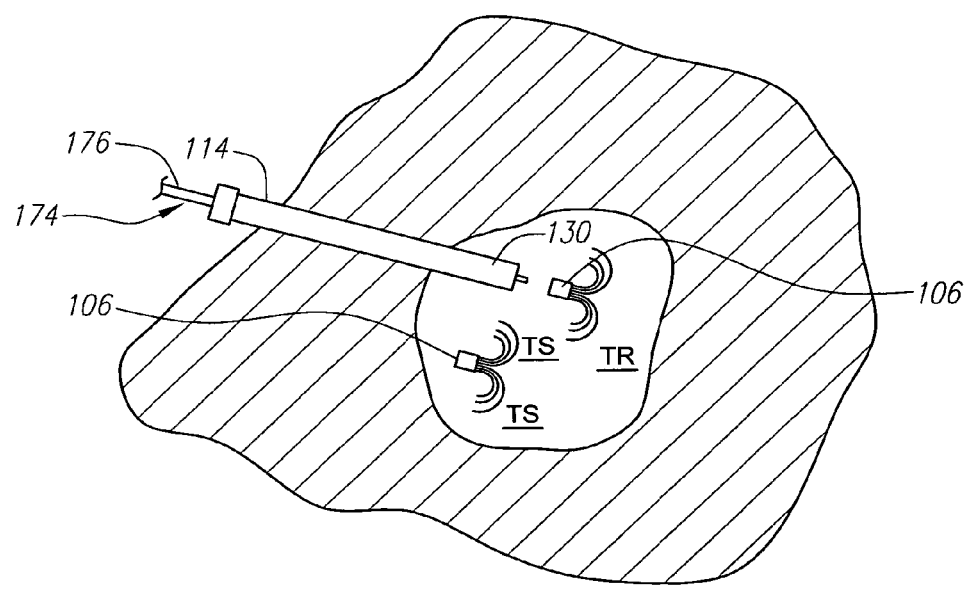

After the cannula 114 is properly placed, multiple electrode devices 106 are sequentially delivered to and distributed throughout the treatment region TR. Specifically, one of the single electrode assemblies 102 is distally advanced through the cannula 114 until the associated needle electrode array 122 deploys radially outward from the distal end 130 of the cannula 114, as shown in FIG. 13C. The delivery device 104, and specifically the core wire 136, will be advanced sufficiently, so that the needle electrode array 122 fully everts in order to maximize the tissue affected by the electrode array 122, as shown in FIG. 13D. Once the electrode device 106 is in its final position, it is then detached from the core wire 136 by conveying electrical energy from the power source (not shown) and through the core wire 136 until the electrolytically detachable junction 142 disintegrates, as shown in FIG. 13E. The detached core wire 136 is then removed from the cannula 114, the cannula 114 is moved to another target TS, and additional delivery/electrode devices 106 are advanced through the cannula 114. The process is repeated until a sufficient number of electrode devices 106 (here, five) are implanted within the treatment region TR, as shown in FIG. 13F. Alternatively, the previously described delivery devices 104 with mechanically detachable junctions (see FIGS. 5-7) can be utilized to deliver the electrode device 106 into the treatment region TR.

Even more alternatively, the multiple electrode delivery devices 174 (see FIG. 8) can be utilized to deliver the electrode devices 106 into the treatment region TR. Specifically, after the cannula 114 is properly placed, the electrode assembly 172 is distally advanced through the cannula 114 until the distal-most needle electrode array 122 deploys radially outward from the distal end 130 of the cannula 114 and fully everts, as shown in FIG. 13C-1. Once the electrode device 106 is in its final position, it is then detached from the core wire 176 by conveying electrical energy from the power source (not shown) and through the core wire 176 until the distal-most electrolytically detachable junction 180 disintegrates, as shown in FIG. 13D-1. The cannula 114 is moved to another target site TS, and the electrode assembly 172 is again distally advanced through the cannula 114 until the next distal-most needle electrode array 122 deploys radially outward from the distal end 130 of the cannula 114, and fully everts, as shown in FIG. 13E-1. Once the electrode device 106 is in its final position, it is then detached from the core wire 176 by conveying electrical energy from the power source (not shown) and through the core wire 176 until the next distal-most electrolytically detachable junction 180 disintegrates, as shown in FIG. 13F-1. Once all of the electrode devices 106 have been implanted into the treatment region, the remaining portion of the core wire 176 is removed from the cannula 114. Alternatively, the previously described multiple electrode delivery devices 184/194 with mechanically detachable junctions (see FIGS. 9 and 10) can be utilized to deliver the electrode devices 106 into the treatment region TR.

Figure 13G:
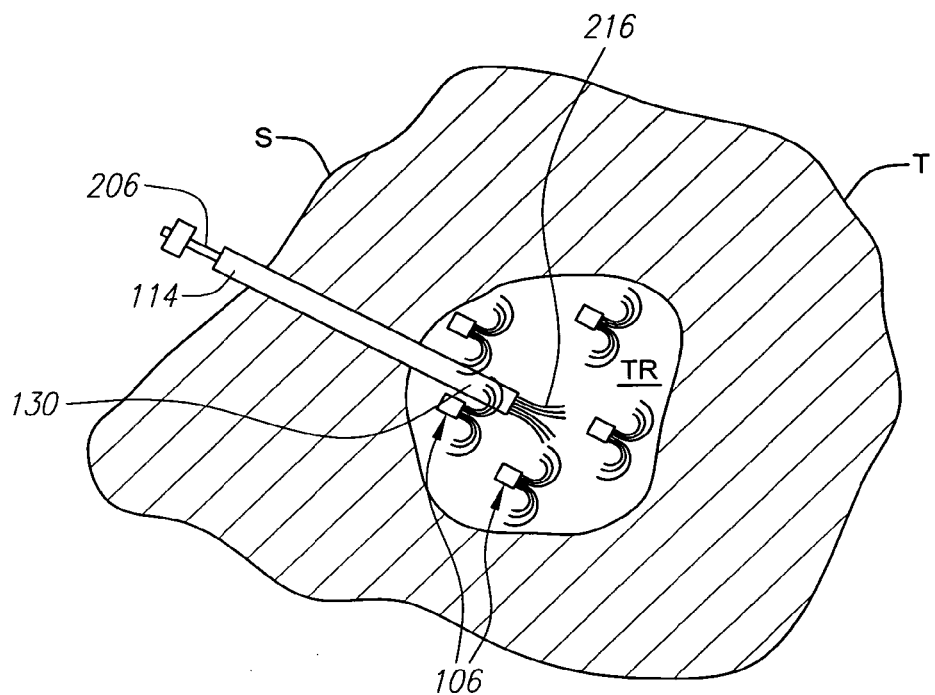
Figure 13H:
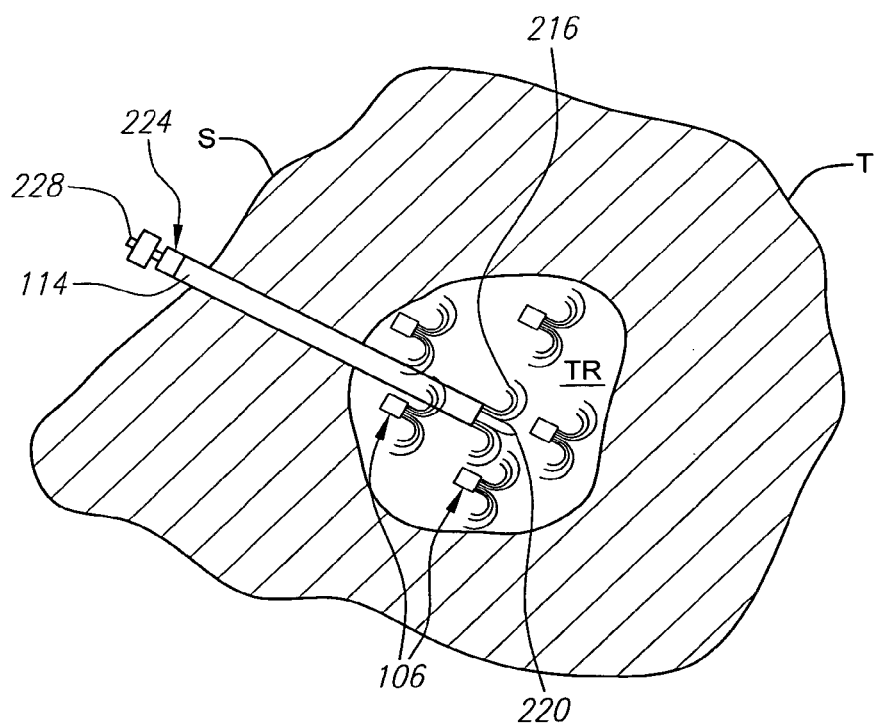

After the electrode devices 106 have been adequately implanted within the treatment region using any of the previously described delivery means, the electrosurgical probe 110 is distally advanced through the cannula 114 to deploy the electrode array 216 radially outward from the distal end 130 of the cannula 114 into the tissue T, as shown in FIG. 13G. Preferably, the electrode device 106 is centered within the implanted electrode devices 106. The shaft 206 will be advanced sufficiently, so that the electrode array 216 fully everts, as shown in FIG. 13H. The sharpened end of the core member 220 facilitates introduction of the electrode array 216 within the treatment region TR.

The RF generator 112 is then connected to the connector assembly 224 via the electrical connector 228, and then operated to convey RF energy from the electrode array 216 of the electrosurgical probe 110 into the tissue T. Because of the electrical conductivity of the tissue T, and through inductance, the implanted electrode devices 106 are indirectly exposed to the RF energy conveyed from the electrode array 216 of the electrosurgical probe 110. Alternatively, the electrode array 216 can directly contact the implanted electrode devices 106, in which case, one or more of the implanted electrode devices 106 can be directly exposed to the RF energy conveyed from the electrode array 216. As a result, RF energy will be distributed throughout the treatment region TR to ablate a greater region than what would be ablated with just the electrode surgical probe 110. If the electrode devices 106 are coated with a therapeutic agent, longer lasting therapy can be provided to the treatment region TR.

Figure 13I:
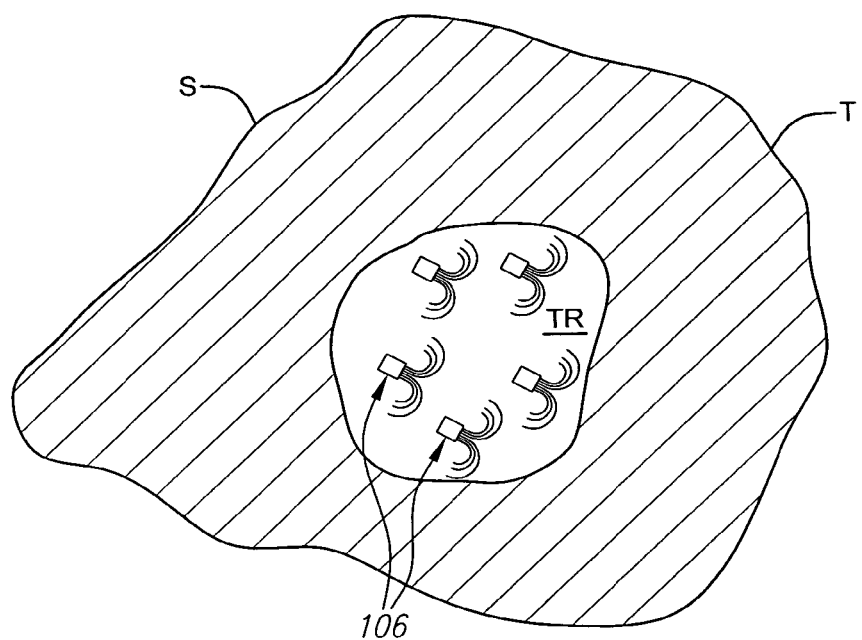

After treatment, the electrosurgical probe 110 and cannula 114 are removed, leaving the electrode arrays 112 implanted within the treatment region TR, as shown in FIG. 13I. The implanted electrode devices 106 provide an additional advantage of creating a roadmap to allow the progress of managing the treatment region TR (e.g., destruction or growth of a tumor) to be tracked during future follow-ups.

Although particular embodiments of the present inventions have been shown and described, it will be understood that it is not intended to limit the present inventions to the preferred embodiments, and it will be obvious to those skilled in the art that various changes and modifications may be made without departing from the spirit and scope of the present inventions. Thus, the present inventions are intended to cover alternatives, modifications, and equivalents, which may be included within the spirit and scope of the present inventions as defined by the claims.

What is claimed is:

1. A tissue ablation system comprising:
    an elongated cannula configured for percutaneous introduction into tissue, the cannula having a proximal end and a distal end and lumen extending between the proximal and distal ends;
    a delivery device slidably disposed in the lumen of the cannula; and
    an electrode device detachably coupled to the delivery device, the electrode device comprising an electrode array.

2. The tissue ablation system of claim 1, further comprising an electrosurgical probe.

3. The tissue ablation system of claim 2, wherein the electrosurgical probe is dimensioned for insertion into a cannula.

4. The tissue ablation system of claim 3, wherein the cannula comprises the same cannula into which the delivery device is slidably disposed.

5. The tissue ablation system of claim 1, wherein the electrode device comprises a connector member and an electrode array coupled thereto.

6. The tissue ablation system of claim 1, wherein the delivery device comprises a core wire, the core wire having an electrolytic detachable junction disposed at a distal end of the core wire.

7. The tissue ablation system of claim 6, further comprising a power source configured to interface with a proximal end of the core wire.

8. The tissue ablation system of claim 1, wherein the delivery device comprises a pusher rod, the electrode device detachably coupled to the pusher rod via a mechanical detachable junction.

9. The tissue ablation system of claim 8, wherein the mechanical detachable junction comprises a threaded arrangement.

10. The tissue ablation system of claim 8, wherein the mechanical detachable junction comprises interlocking clasps.

11. The tissue ablation system of claim 8, wherein the mechanical detachable junction comprises a spherical element disposed at a distal end of the pusher rod and a pair of spherical elements disposed at a proximal end of a connector member operatively coupled to the electrode device.

12. A tissue ablation system comprising:
    an elongated cannula configured for percutaneous introduction into tissue, the cannula having a proximal end and a distal end and lumen extending between the proximal and distal ends;
    a core wire slidably disposed in the lumen of the cannula; and
    a plurality of electrode devices detachably coupled to the core wire at a plurality of locations.

13. The tissue ablation system of claim 12, further comprising a power source operatively coupled to a proximal end of the core wire.

14. The tissue ablation system of claim 12, further comprising an electrosurgical probe.

15. The tissue ablation system of claim 14, wherein the electrosurgical probe is dimensioned for insertion into a cannula.

16. The tissue ablation system of claim 12, wherein the cannula comprises the same cannula into which the delivery device is slidably disposed.

17. The tissue ablation system of claim 12, wherein the electrode device comprises a connector member and an electrode array coupled thereto.

18. A tissue ablation system comprising:
    an elongated cannula configured for percutaneous introduction into tissue, the cannula having a proximal end and a distal end and lumen extending between the proximal and distal ends;
    a pusher rod slidably disposed in the lumen of the cannula; and
    a plurality of electrode devices detachably coupled to the pusher rod at a plurality of locations, wherein adjacent electrode devices are coupled via rod segments that interface in a mechanical detachable junction.

19. The tissue ablation system of claim 18, wherein the mechanical detachable junction comprises a threaded arrangement.

20. The tissue ablation system of claim 18, wherein the mechanical detachable junction comprises interlocking clasps.

21. The tissue ablation system of claim 18, wherein the mechanical detachable junction comprises a plurality of interlocking spherical elements.

* * * * *